United States Patent
Wham et al.

(10) Patent No.: US 8,685,016 B2
(45) Date of Patent: *Apr. 1, 2014

(54) SYSTEM AND METHOD FOR TISSUE SEALING

(75) Inventors: Roberth H. Wham, Boulder, CO (US);
Rebecca Coulson, Lyons, CO (US);
Kari L. Riegner, Golden, CO (US);
David A. Schechter, Longmont, CO (US); Nicole McKenna, Boulder, CO (US); Barbara R. Bastian, Erie, CO (US); Jennifer S. Harper, Westminster, CO (US)

(73) Assignee: Covidien AG (CH)

( * ) Notice: Subject to any disclaimer, the term of this patent is extended or adjusted under 35 U.S.C. 154(b) by 699 days.

This patent is subject to a terminal disclaimer.

(21) Appl. No.: 12/390,944

(22) Filed: Feb. 23, 2009

(65) Prior Publication Data

US 2009/0157071 A1    Jun. 18, 2009

Related U.S. Application Data

(63) Continuation-in-part of application No. 11/657,170, filed on Jan. 24, 2007, now Pat. No. 7,972,328.

(60) Provisional application No. 60/761,443, filed on Jan. 24, 2006.

(51) Int. Cl.
*A61B 18/04* (2006.01)
*A61B 18/18* (2006.01)

(52) U.S. Cl.
USPC .............................. 606/38; 606/51

(58) Field of Classification Search
USPC .................................................. 606/32–51
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

International Search Report EP 10001808 dated Jun. 21, 2010.

(Continued)

*Primary Examiner* — Matthew F DeSanto

(57) ABSTRACT

An electrosurgical system is disclosed. The electrosurgical system includes an electrosurgical generator adapted to supply electrosurgical energy to tissue. The electrosurgical generator includes impedance sensing circuitry which measures impedance of tissue, a processor configured to determine whether a tissue reaction has occurred as a function of a minimum impedance value and a predetermined rise in impedance, wherein tissue reaction corresponds to a boiling point of tissue fluid, and an electrosurgical instrument including at least one active electrode adapted to apply electrosurgical energy to tissue. A tissue cooling period is provided to enhance operative outcomes.

25 Claims, 8 Drawing Sheets

(56) References Cited

U.S. PATENT DOCUMENTS

| | | |
|---|---|---|
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |

(56) References Cited

U.S. PATENT DOCUMENTS

| | | |
|---|---|---|
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,067,953 A | 11/1991 | Feucht |
| 5,075,839 A | 12/1991 | Fisher et al. |
| 5,087,257 A | 2/1992 | Farin |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,234,427 A | 8/1993 | Ohtomo et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson |
| 5,433,739 A | 7/1995 | Sluijter et al. |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,496,312 A | 3/1996 | Klicek |
| 5,496,313 A | 3/1996 | Gentelia et al. |
| 5,496,314 A | 3/1996 | Eggers |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa |
| 5,540,684 A | 7/1996 | Hassler, Jr. |
| 5,541,376 A | 7/1996 | Ladtkow et al. |
| 5,545,161 A | 8/1996 | Imran |
| 5,556,396 A | 9/1996 | Cohen et al. |
| 5,558,671 A | 9/1996 | Yates |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |

(56) References Cited

U.S. PATENT DOCUMENTS

| | | |
|---|---|---|
| 5,693,042 A | 12/1997 | Boiarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern |
| 5,766,153 A | 6/1998 | Eggers et al. |
| 5,766,165 A | 6/1998 | Gentelia et al. |
| 5,769,847 A | 6/1998 | Panescu |
| 5,772,659 A | 6/1998 | Becker et al. |
| 5,788,688 A | 8/1998 | Bauer et al. |
| 5,792,138 A | 8/1998 | Shipp |
| 5,797,902 A | 8/1998 | Netherly |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Bussey et al. |
| 5,830,212 A | 11/1998 | Cartmell |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A * | 2/1999 | Kannenberg et al. ............ 606/34 |
| 5,891,142 A | 4/1999 | Eggers et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,959,253 A | 9/1999 | Shinchi |
| 5,961,344 A | 10/1999 | Rosales et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,022,346 A | 2/2000 | Panescu et al. |
| 6,022,347 A | 2/2000 | Lindenmeier et al. |
| 6,033,399 A * | 3/2000 | Gines ............................ 606/38 |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,093,186 A | 7/2000 | Goble |
| 6,102,497 A | 8/2000 | Ehr et al. |
| 6,102,907 A | 8/2000 | Smethers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven |
| 6,123,701 A | 9/2000 | Nezhat |
| 6,123,702 A | 9/2000 | Swanson et al. |
| 6,132,429 A | 10/2000 | Baker |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,171,304 B1 | 1/2001 | Netherly et al. |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,261,285 B1 | 7/2001 | Novak |
| 6,261,286 B1 | 7/2001 | Goble et al. |
| 6,267,760 B1 | 7/2001 | Swanson |
| 6,273,886 B1 | 8/2001 | Edwards et al. |

(56) References Cited

U.S. PATENT DOCUMENTS

| | | |
|---|---|---|
| 6,275,786 B1 | 8/2001 | Daners |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,364,877 B1 | 4/2002 | Goble et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 6,989,010 B2 | 1/2006 | Francischelli et al. |

(56) References Cited

U.S. PATENT DOCUMENTS

| | | |
|---|---|---|
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 2003/0181898 A1 | 9/2003 | Bowers |
| 2003/0199863 A1 | 10/2003 | Swanson |
| 2004/0015159 A1 | 1/2004 | Slater et al. |
| 2004/0030330 A1 | 2/2004 | Brassell et al. |
| 2004/0068304 A1 | 4/2004 | Paton |
| 2004/0097912 A1 | 5/2004 | Gonnering |
| 2004/0143263 A1 | 7/2004 | Schechter et al. |
| 2004/0172016 A1 | 9/2004 | Bek et al. |
| 2004/0193148 A1* | 9/2004 | Wham et al. ............ 606/40 |
| 2004/0215183 A1* | 10/2004 | Hoey et al. ............. 606/34 |
| 2005/0004564 A1 | 1/2005 | Wham |
| 2005/0004634 A1 | 1/2005 | Ricart et al. |
| 2005/0021020 A1 | 1/2005 | Blaha et al. |
| 2005/0101949 A1 | 5/2005 | Harano et al. |
| 2005/0109111 A1 | 5/2005 | Manlove et al. |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2006/0291178 A1 | 12/2006 | Shih |
| 2007/0038209 A1 | 2/2007 | Buysse et al. |
| 2007/0066969 A1 | 3/2007 | McGreevy |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173811 A1 | 7/2007 | Couture et al. |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |

(56) References Cited

U.S. PATENT DOCUMENTS

| | | |
|---|---|---|
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |
| 2011/0144635 A1 | 6/2011 | Harper et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1707144 | 3/2006 |
| EP | 1645235 | 4/2006 |
| EP | 880220 | 6/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1810634 | 7/2007 |
| EP | 1854423 | 11/2007 |
| EP | 1862137 | 12/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO9710763 | 3/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO02/00129 | 1/2002 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060365 | 7/2005 |
| WO | WO2005/060849 | 7/2005 |
| WO | WO2006/050888 | 5/2006 |
| WO | WO2006/105121 | 10/2006 |

OTHER PUBLICATIONS

U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.

(56) References Cited

OTHER PUBLICATIONS

U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied.Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
European Search Report EP 10 18 1060, dated Jan. 17, 2011.
European Search Report for EP 13 16 9684 dated Aug. 27, 2013.
US 6,878,148, 04/2005, Goble et al. (withdrawn)

\* cited by examiner

SYSTEM AND METHOD FOR TISSUE SEALING

CROSS-REFERENCE TO RELATED APPLICATIONS

This application is a continuation-in-part of commonly-owned U.S. patent application Ser. No. 11/657,170, filed Jan. 24, 2007, now U.S. Pat. No. 7,972,328, which claims priority to U.S. Provisional Application Ser. No. 60/761,443, filed Jan. 24, 2006, the entirety of each being hereby incorporated by reference for all purposes.

BACKGROUND

1. Technical Field

The present disclosure relates to an electrosurgical system and method for performing electrosurgical procedures. More particularly, the present disclosure relates to sealing tissue, wherein energy is administered to match measured impedance to a desired impedance, and a tissue cooling time is observed prior to the completion of the seal.

2. Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode (e.g., a return pad) carries the current back to the generator. In monopolar electrosurgery, the source electrode is typically part of the surgical instrument held by the surgeon and applied to the tissue to be treated. The patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive plates which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing sealing plates). In addition, electrosurgical energy must be applied to the tissue under controlled conditions to ensure creation of an effective vessel seal. Techniques have been developed whereby the energy applied to the tissue is varied during the tissue sealing process to achieve a desired tissue impedance trajectory. When a target tissue impedance threshold is reached, the tissue seal is deemed completed and the delivery of electrosurgical energy is halted.

SUMMARY

The present disclosure relates to a vessel or tissue sealing system and method. In particular, the system discloses an electrosurgical instrument, which may be a bipolar forceps having two jaw members configured for grasping tissue. Each of the jaw members may include a sealing plate which communicates electrosurgical energy to the tissue. At the start of the procedure, the system may transmit an initial interrogatory pulse for determining initial tissue impedance. Additionally or alternatively at the start of the procedure, the system may identify characteristics of the electrosurgical instrument. The system determines whether tissue reaction has occurred and calculates the desired impedance trajectory. The system calculates a target impedance value at each time step based on a predefined desired rate of change of impedance. The system then controls measured tissue impedance to match target impedance. The system may sense parameters related to the sealing process. For example without limitation, the system may sense a temperature, a tissue type, and/or a fluid type. Additionally or alternatively, the system may determine an aggregate amount of energy delivered during the sealing process. The delivery of energy may be halted when the measured impedance is above threshold for a predetermined period of time. The threshold is defined as a specified impedance level above the initial measured impedance value.

After the delivery of energy is halted, the system may provide a tissue cooling time. The cooling time may allow reformed collagen within the fused tissue to solidify, or set in place, between the jaw members. The cooling time may promote denaturation of collagen. The cooling time may be any duration of time, such as a fixed period of time, or an adaptive time, which is dependent upon parameters relating to the tissue fusion (sealing) process, for example without limitation, tissue temperature, tissue impedance, tissue mass, energy delivery, and/or instrument characteristics. Upon expiration of a cooling period the sealing process is completed. The system may provide an indication that the end of the sealing process is completed, such as an audible sound (i.e., "endtone"), whereupon the user may release the jaws.

During the cooling time, cooling of tissue may be effectuated by conduction, i.e., residual heat from fused tissue is drawn away from the tissue by, for example without limitation, the instrument jaws, surrounding tissue, or surrounding fluids such as blood or saline. In embodiments, a coolant, such as saline, may be introduced to the surgical site to promote cooling. It is further envisioned that active cooling elements may be included in the disclosed system, for example without limitation, heat pipes, cooling jackets, and thermoelectric (Peltier effect) devices.

In embodiments, it is envisioned that an initial "baseline" cooling time is established. The baseline "cool-down" time may be dependent upon a sealing process parameter that is determined during sealing process initialization, for example without limitation, an initial tissue impedance measurement, an initial temperature, an initial fluid measurement, and/or a property of the forceps or instrument (i.e., jaw size, jaw angle, instrument type, thermal coefficients, and the like).

According to one aspect of the present disclosure, an electrosurgical system is disclosed. The electrosurgical system includes an electrosurgical generator adapted to supply electrosurgical energy to tissue. The electrosurgical generator may include impedance sensing circuitry which measures impedance of tissue, a processor configured to determine whether a tissue reaction has occurred as a function of a minimum impedance value and a predetermined rise in impedance, wherein tissue reaction corresponds to a boiling point of tissue fluid, and an electrosurgical instrument including at least one active electrode adapted to apply electrosurgical energy to tissue. The electrosurgical generator may include temperature sensing circuitry and/or fluid sensing circuitry. Additionally or alternatively, the electrosurgical generator may include circuitry for identifying characteristics of an electrosurgical instrument coupled thereto. The electrosurgical instrument may include an identification module to enable the electrosurgical generator to identify the instrument. For example without limitation, the identification module may include at least one resistive element have a resistance value corresponding to a characteristic of the instrument, such as the instrument configuration (i.e., model number), a unique instrument identifier (i.e., serial number) and/or a thermal property of the jaws. In embodiments, the identification module may include computer memory (i.e., read-only memory or flash memory), RFID tag, optical tag (i.e., barcode), or other encoding as will be familiar to the skilled artisan. In embodiments, the instrument includes a sensor in operable communication with the generator that is configured to sense the included angle between the jaws, which angle may be indicative of the size and/or mass of tissue held therebetween. The generator may use an algorithm or a lookup table to determine a desired cool-down time based upon the identification module.

According to another aspect of the present disclosure, an electrosurgical generator is disclosed. The electrosurgical generator includes an RF output stage adapted to supply electrosurgical energy to tissue and impedance sensing circuitry which measures impedance of tissue. The generator also includes a processor configured to determine whether tissue reaction has occurred as a function of a minimum impedance value and a predetermined rise in impedance, wherein tissue reaction corresponds to a boiling point of tissue fluid. The processor may be configured to generate a target impedance trajectory as a function of measured impedance and desired rate of change based on the tissue reaction determination, wherein the target impedance trajectory includes a plurality of target impedance values. The generator may include an electrosurgical instrument including at least one active electrode adapted to apply electrosurgical energy to tissue. The processor may be configured to determine the duration of a cooling time in accordance with, for example without limitation, characteristics of the electrosurgical instrument, tissue properties (i.e., impedance, temperature), surgical site properties (i.e., presence of fluid at the site), an amount of energy delivered to tissue (i.e., net energy delivery), jaw angle (i.e., the included angle between the opposing jaw members), and/or operator-entered parameters.

A method for performing an electrosurgical procedure is also contemplated according to the present disclosure. The method includes the steps of grasping tissue between the jaws of an electrosurgical instrument, applying electrosurgical energy at an output level to tissue from an electrosurgical generator, determining whether tissue reaction has occurred as a function of a minimum impedance value and a predetermined rise in impedance, wherein tissue reaction corresponds to a boiling point of tissue fluid, generating a target impedance trajectory as a function of measured impedance and desired rate of change based on the tissue reaction determination, the target impedance trajectory including a plurality of target impedance values, discontinuing the application of electrosurgical energy to tissue, allowing tissue to cool down during a cooling period, and releasing tissue from the jaws of the electrosurgical instrument. In embodiments, the method includes the steps of sensing the included angle formed by the jaw members and adjusting energy delivery and/or cooling period time in accordance therewith.

BRIEF DESCRIPTION OF THE DRAWINGS

The above and other aspects, features, and advantages of the present disclosure will become more apparent in light of the following detailed description when taken in conjunction with the accompanying drawings wherein.

DETAILED DESCRIPTION

Figure 1:
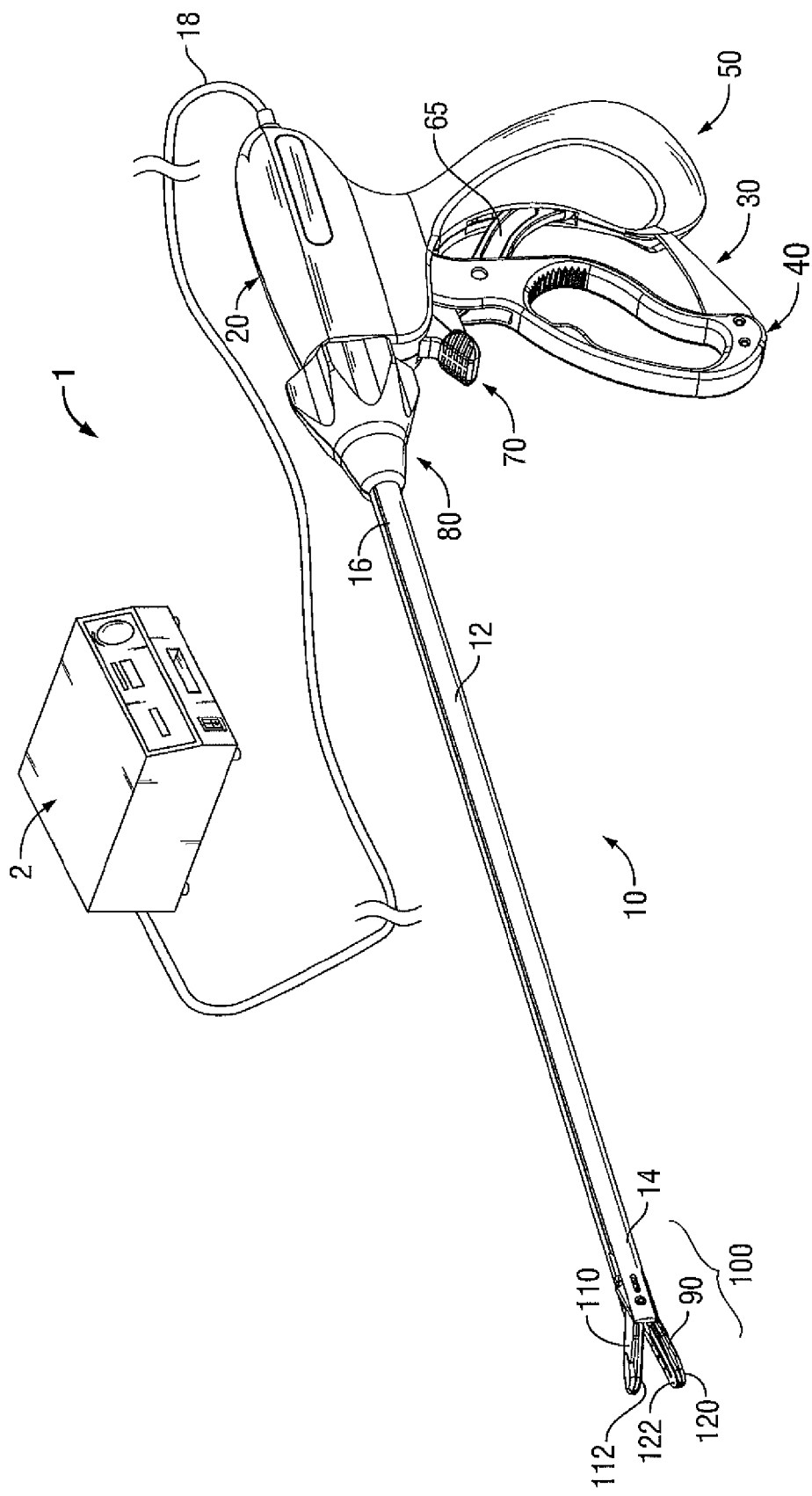
FIG. 1 is a perspective view of one embodiment of an electrosurgical system according to the present disclosure.

Particular embodiments of the present disclosure will be described hereinbelow with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument, laparoscopic instrument, or an open instrument. It should also be appreciated that different electrical and mechanical connections and other considerations may apply to each particular type of instrument, however, the novel aspects with respect to vessel and tissue sealing are generally consistent with respect to both the open or endoscopic designs.

In the drawings and in the description which follows, the term "proximal" refers to the end of the forceps 10 which is closer to the user, while the term "distal" refers to the end of the forceps which is further from the user.

FIG. 1 is a schematic illustration of an electrosurgical system 1. The system 1 includes an electrosurgical forceps 10 for treating patient tissue. Electrosurgical RF energy is supplied to the forceps 10 by a generator 2 via a cable 18 thus allowing the user to selectively coagulate and/or seal tissue.

As shown in FIG. 1, the forceps 10 is an endoscopic version of a vessel sealing bipolar forceps. The forceps 10 is configured to support an effector assembly 100 and generally includes a housing 20, a handle assembly 30, a rotating assembly 80, and a trigger assembly 70 which mutually cooperate with the end effector assembly 100 to grasp, seal and, if required, divide tissue. Forceps 10 also includes a shaft 12 which has a distal end 14 which mechanically engages the end effector assembly 100 and a proximal end 16 which mechanically engages the housing 20 proximate the rotating assembly 80.

Figure 3:
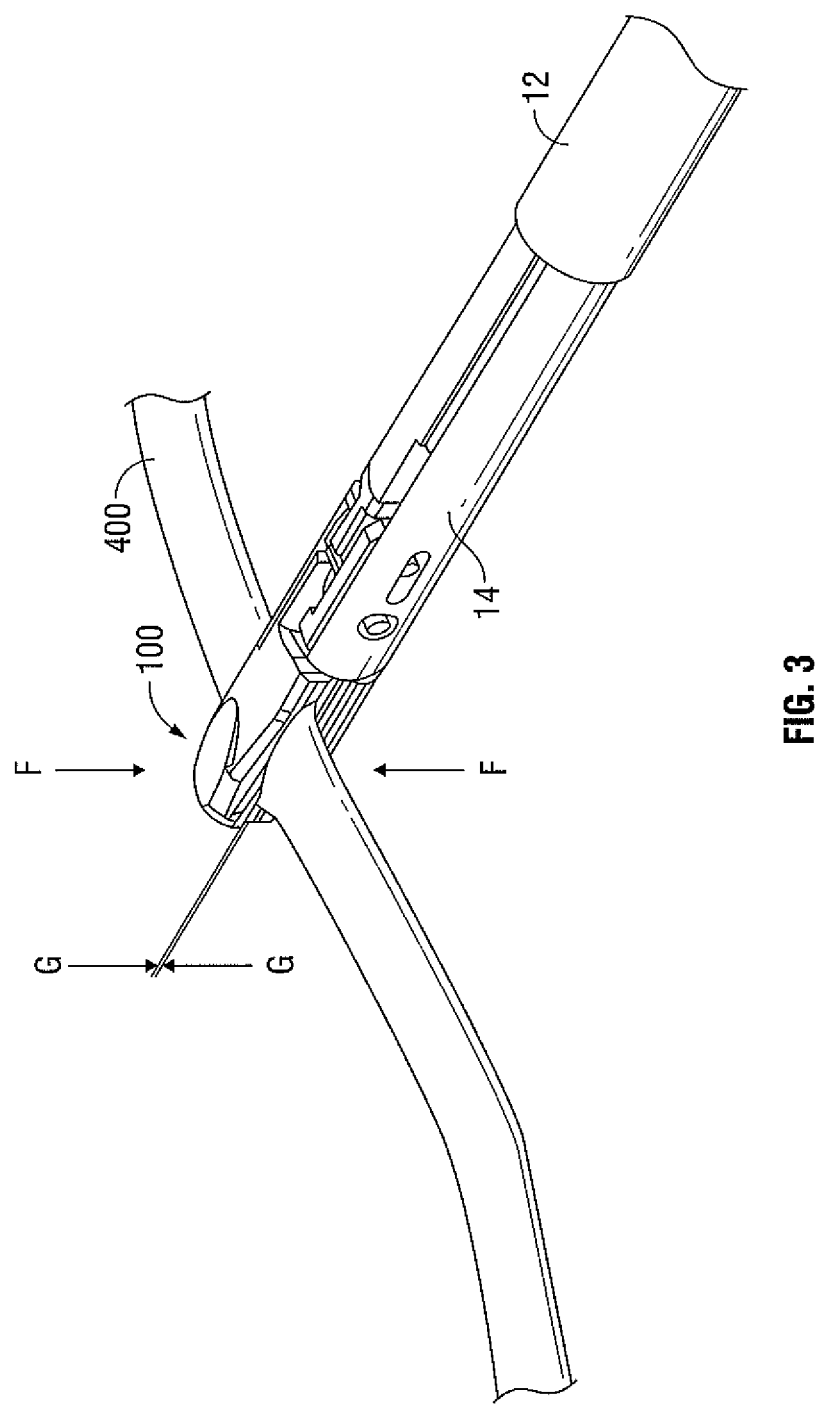
FIG. 3 is a rear, perspective view of the end effector of FIG. 1 shown with tissue grasped therein.

The forceps 10 also includes a plug (not shown) which connects the forceps 10 to a source of electrosurgical energy, e.g., generator 2, via cable 18. Handle assembly 30 includes a fixed handle 50 and a movable handle 40. Handle 40 moves relative to the fixed handle 50 to actuate the end effector assembly 100 and enable a user to selectively grasp and manipulate tissue 400 as shown in FIG. 3. Forceps 10 may also include an identification module (not explicitly shown) such as a resistor or computer memory readable by the generator 2 to identify the forceps.

Figure 4:
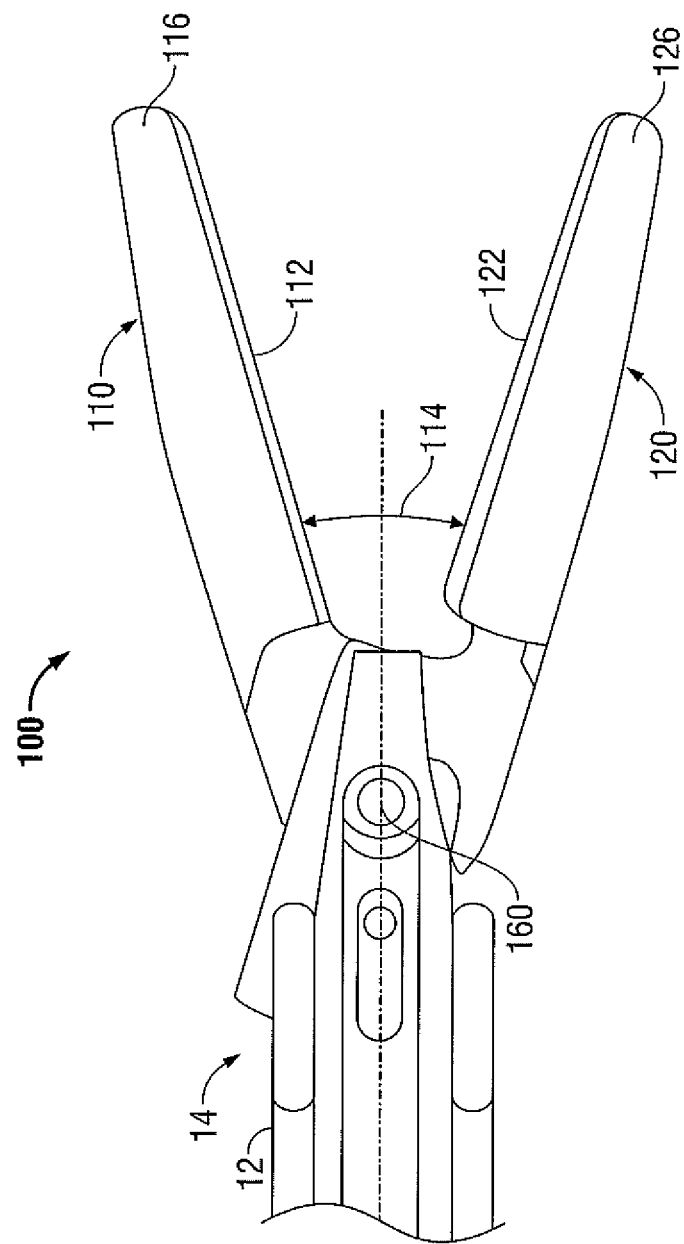
FIG. 4 is a side, partial internal view of an endoscopic forceps according to the present disclosure.

Referring to FIGS. 1, 3 and 4, end effector assembly 100 includes a pair of opposing jaw members 110 and 120 each having an electrically conductive sealing plate 112 and 122, respectively, attached thereto for conducting electrosurgical energy through tissue 400 held therebetween. More particularly, the jaw members 110 and 120 move in response to movement of handle 40 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto. In embodiments, end effector assembly 100 includes a jaw angle sensor (now explicitly shown) that is adapted to sense the included angle 114 between opposing jaw members 110 and 120 and is configured to operably couple to generator 2.

Jaw members 110 and 120 are activated using a drive assembly (not shown) enclosed within the housing 20. The drive assembly cooperates with the movable handle 40 to impart movement of the jaw members 110 and 120 from the open position to the clamping or closed position. Examples of a handle assemblies are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 entitled "VESSEL SEALER AND DIVIDER FOR USE WITH SMALL TROCARS AND CANNULAS" which are both hereby incorporated by reference herein in their entirety.

Jaw members 110 and 120 also include outer housings on insulators 116 and 126 which together with the dimension of the conductive plates of the jaw members 110 and 120 are configured to limit and/or reduce many of the known undesirable effects related to tissue sealing, e.g., flashover, thermal spread and stray current dissipation.

In addition, the handle assembly 30 of the present disclosure may include a four-bar mechanical linkage which provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing plates 112 and 122 in a closed position against the tissue. The details relating to the inter-cooperative relationships of the inner-working components of forceps 10 are disclosed in the above-cited commonly-owned U.S. patent application Ser. No. 10/369,894. Another example of an endoscopic handle assembly which discloses an off-axis, lever-like handle assembly, is disclosed in the above-cited U.S. patent application Ser. No. 10/460,926.

The forceps 10 also includes a rotating assembly 80 mechanically associated with the shaft 12 and the drive assembly (not shown). Movement of the rotating assembly 80 imparts similar rotational movement to the shaft 12 which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 1 and 4, end effector assembly 100 attaches to the distal end 14 of shaft 12. The jaw members 110 and 120 are pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 20 and handle assembly 30. In either of these two instances, the forceps 10 may be either partially disposable or replaceable, such as where a new or different end effector assembly 100 or end effector assembly 100 and shaft 12 are used to selectively replace the old end effector assembly 100 as needed.

The generator 2 includes input controls (e.g., buttons, activators, switches, touch screen, etc.) for controlling the generator 2. In addition, the generator 2 includes one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., coagulating, tissue sealing, division with hemostatis, etc.). It is also envisioned that the forceps 10 may include a plurality of input controls which may be redundant with certain input controls of the generator 2. Placing the input controls at the forceps 10 allows for easier and faster modification of RF energy parameters during the surgical procedure without requiring interaction with the generator 2.

Figure 2:
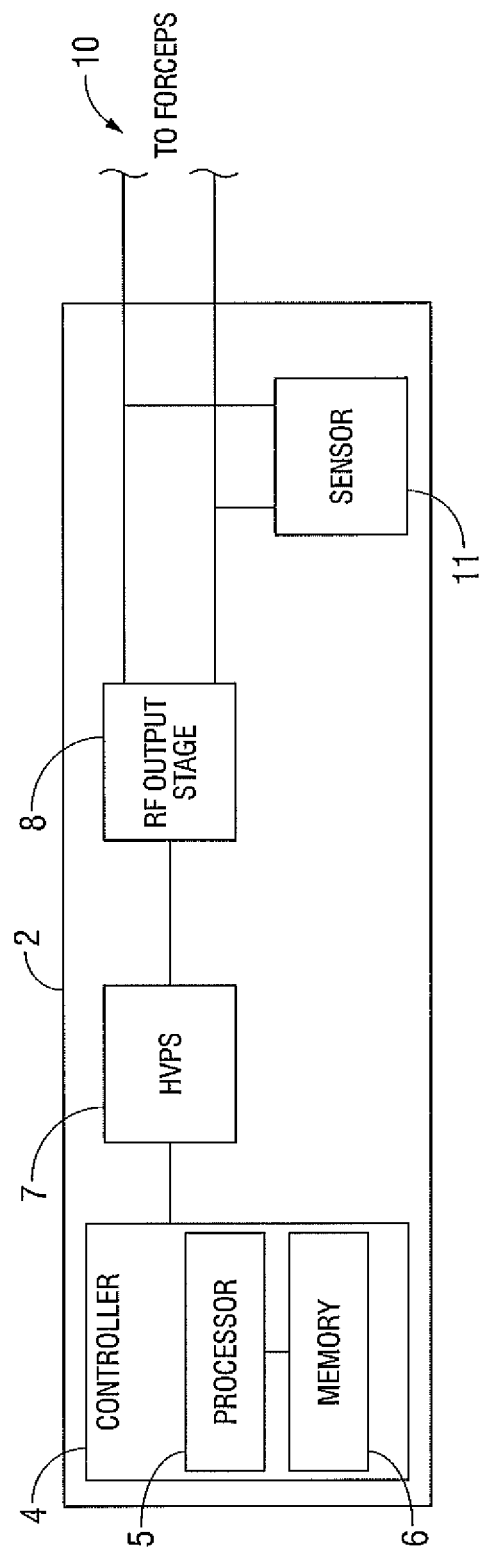
FIG. 2 is a schematic block diagram of a generator algorithm according to the present disclosure.

FIG. 2 shows a schematic block diagram of the generator 2 having a controller 4, a high voltage DC power supply 7 ("HVPS"), an RF output stage 8, and a sensor circuitry 11. The DC power supply 7 provides DC power to an RF output stage 8 which then converts DC power into RF energy and delivers the RF energy to the forceps 10. The controller 4 includes a processor 5 operably connected to a memory 6 which may be volatile type memory (e.g., RAM) and/or non-volatile type memory (e.g., flash media, disk media, etc.). The processor 5 includes an output port which is operably connected to the HVPS 7 and/or RF output stage 8 allowing the processor 5 to control the output of the generator 2 according to either open and/or closed control loop schemes. A closed loop control scheme may be a feedback control loop wherein the sensor circuitry 11 provides feedback to the controller 4

(i.e., information obtained from one or more of sensing mechanisms for sensing various tissue parameters such as tissue impedance, tissue temperature, fluid presence, output current and/or voltage, etc.). The controller 4 then signals the HVPS 7 and/or RF output stage 8 which then adjusts DC and/or RF power supply, respectively. The controller 4 also receives input signals from the input controls of the generator 2 and/or forceps 10. The controller 4 utilizes the input signals to adjust the power output of the generator 2 and/or instructs the generator 2 to perform other control functions.

It is known that sealing of the tissue 400 is accomplished by virtue of a unique combination of gap control, pressure and electrical control. In other words, controlling the intensity, frequency and duration of the electrosurgical energy applied to the tissue through the sealing plate 112 and 122 are important electrical considerations for sealing tissue. In addition, two mechanical factors play an important role in determining the resulting thickness of the sealed tissue and the effectiveness of the seal, i.e., the pressure applied between the opposing jaw members 110 and 120 (between about 3 kg/cm2 to about 16 kg/cm2) and the gap distance "G" between the opposing sealing plates 112 and 122 of the jaw members 110 and 120, respectively, during the sealing process (between about 0.001 inches to about 0.006 inches). One or more stop members 90 may be employed on one or both sealing plates to control the gap distance. A third mechanical factor has recently been determined to contribute to the quality and consistency of a tissue seal, namely the closure rate of the electrically conductive surfaces or sealing plates during electrical activation.

Since the forceps 10 applies energy through electrodes, each of the jaw members 110 and 120 includes a pair of electrically sealing plates 112, 122 respectively, disposed on an inner-facing surface thereof. Thus, once the jaw members 110 and 120 are fully compressed about the tissue 400, the forceps 10 is now ready for selective application of electrosurgical energy as shown in FIG. 4. At that point, the electrically sealing plates 112 and 122 cooperate to seal tissue 400 held therebetween upon the application of electrosurgical energy.

The system 1 according to the present disclosure regulates application of energy and pressure to achieve an effective seal capable of withstanding high burst pressures. The generator 2 applies energy to tissue at constant current based on the current control curve of FIG. 8 which is discussed in more detail below. Energy application is regulated by the controller 4 pursuant to an algorithm stored within the memory 6. The algorithm maintains energy supplied to the tissue at constant voltage. The algorithm varies output based on the type of tissue being sealed. For instance, thicker tissue typically requires more power, whereas thinner tissue requires less power. Therefore, the algorithm adjusts the output based on tissue type by modifying specific variables (e.g., voltage being maintained, duration of power application etc.). In embodiments, the algorithm adjusts the output based on jaw angle.

As mentioned above, various methods and devices are contemplated to automatically regulate the closure of the jaw members 110 and 120 about tissue to keep the pressure constant during the sealing process. For example, the forceps 10 may be configured to include a ratchet mechanism (not explicitly shown) which initially locks the jaw members 110 and 120 against the tissue under a desired tissue pressure and then increases the pressure according to the command from the processor 5 to an optimum tissue pressure. The ratchet mechanism (not explicitly shown) is configured to adjust the pressure based on electrical activation and/or the tissue reaction. It is also envisioned that the pressure may be controlled in a similar manner towards the end of the seal cycle, i.e., release pressure. The pressure may be held constant or varied during a cooling period. A similar or the same ratchet mechanism (not explicitly shown) may be employed for this purpose as well. The ratchet mechanism (not explicitly shown) may be configured to automatically release or unlock at the end of a cooling period. Other controllable closure mechanisms or pressure-applying mechanism are also envisioned which may be associated with the handle assembly 30, the housing 20 and/or the jaw members 110 and 120. Any of these mechanisms may be housed in the housing 20 or form a part of each particular structure. The ratchet, closure, and/or pressure-applying mechanism may include any suitable actuating device, for example without limitation, a solenoid, stepper motor, vacuum actuator, and/or a pressure actuator.

It is also envisioned that one or more stop members 90 may be selectively controllable to regulate the closure pressure and gap distance to affect the seal. Commonly-owned U.S. application Ser. No. 10/846,262 describes one such variable stop system which may be used for this purpose, the entire contents being incorporated by reference herein.

Figure 5:
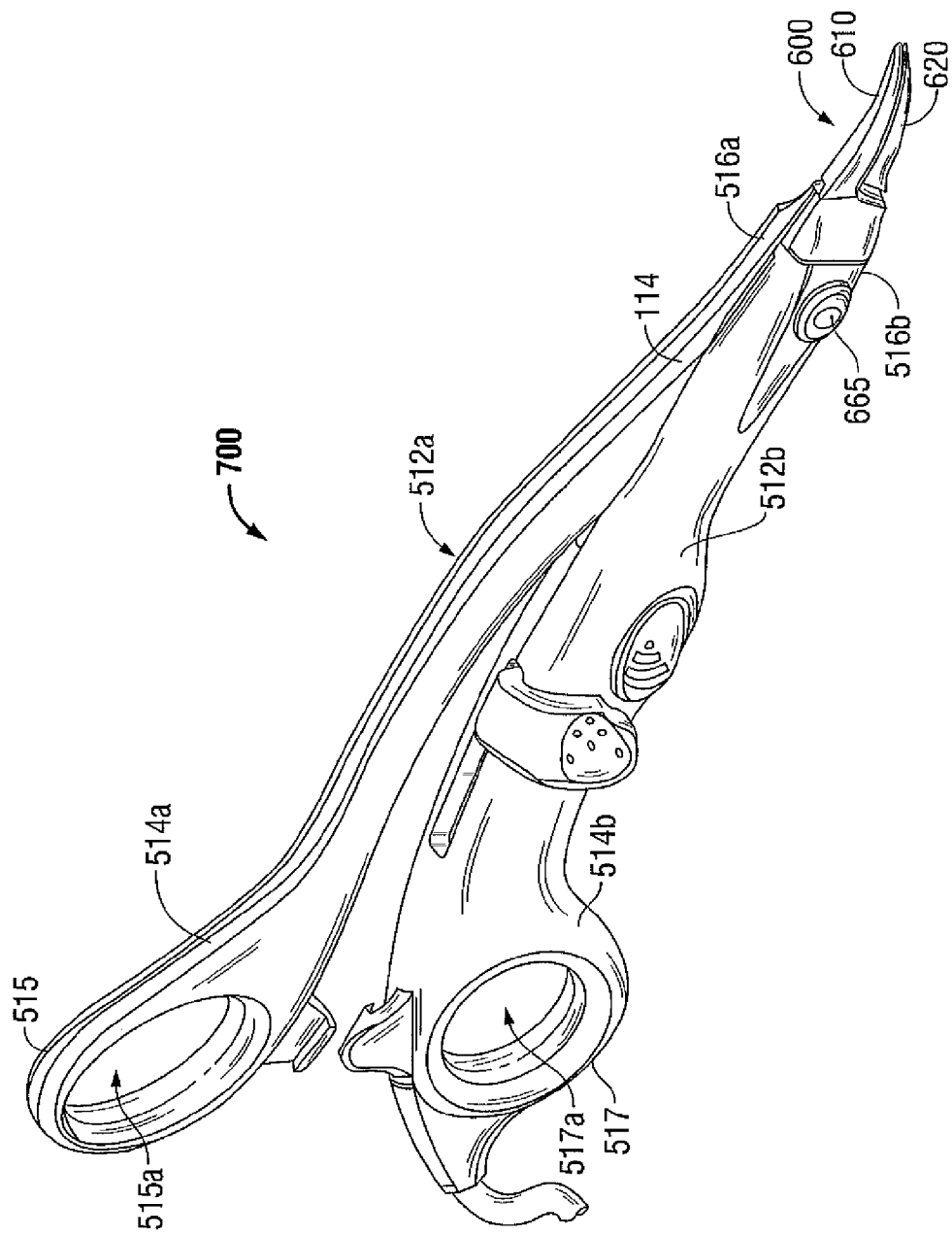
FIG. 5 is a perspective view of an open bipolar forceps according to the present disclosure.

From the foregoing and with reference to the various figure drawings, those skilled in the art will appreciate that certain modifications can also be made to the present disclosure without departing from the scope of the same. For example and as mentioned above, it is contemplated that any of the various jaw arrangements disclosed herein may be employed on an open forceps such as the open forceps 700 shown in FIG. 5. The forceps 700 includes an end effector assembly 600 which is attached to the distal ends 516a and 516b of shafts 512a and 512b, respectively. The end effector assembly 600 includes a pair of opposing jaw members 610 and 620 which are pivotally connected about a pivot pin 665 and which are movable relative to one another to grasp vessels and/or tissue. Each of the opposing jaw members 610, 620 includes electrically sealing plates 112, 122 which allow the open forceps 700 to be used for clamping tissue for sealing.

Each shaft 512a and 512b includes a handle 515 and 517, respectively, disposed at the proximal end 514a and 514b thereof which each define a finger hole 515a and 517a, respectively, therethrough for receiving a finger of the user. Finger holes 515a and 517a facilitate movement of the shafts 512a and 512b relative to one another which, in turn, pivot the jaw members 610 and 620 from an open position wherein the jaw members 610 and 620 are disposed in spaced relation relative to one another to a clamping or closed position wherein the jaw members 610 and 620 cooperate to grasp tissue or vessels therebetween. Further details relating to one particular open forceps are disclosed in commonly-owned U.S. application Ser. No. 10/962,116 filed Oct. 8, 2004 entitled "OPEN VESSEL SEALING INSTRUMENT WITH CUTTING MECHANISM AND DISTAL LOCKOUT", the entire contents of which being incorporated by reference herein.

Figure 6A:
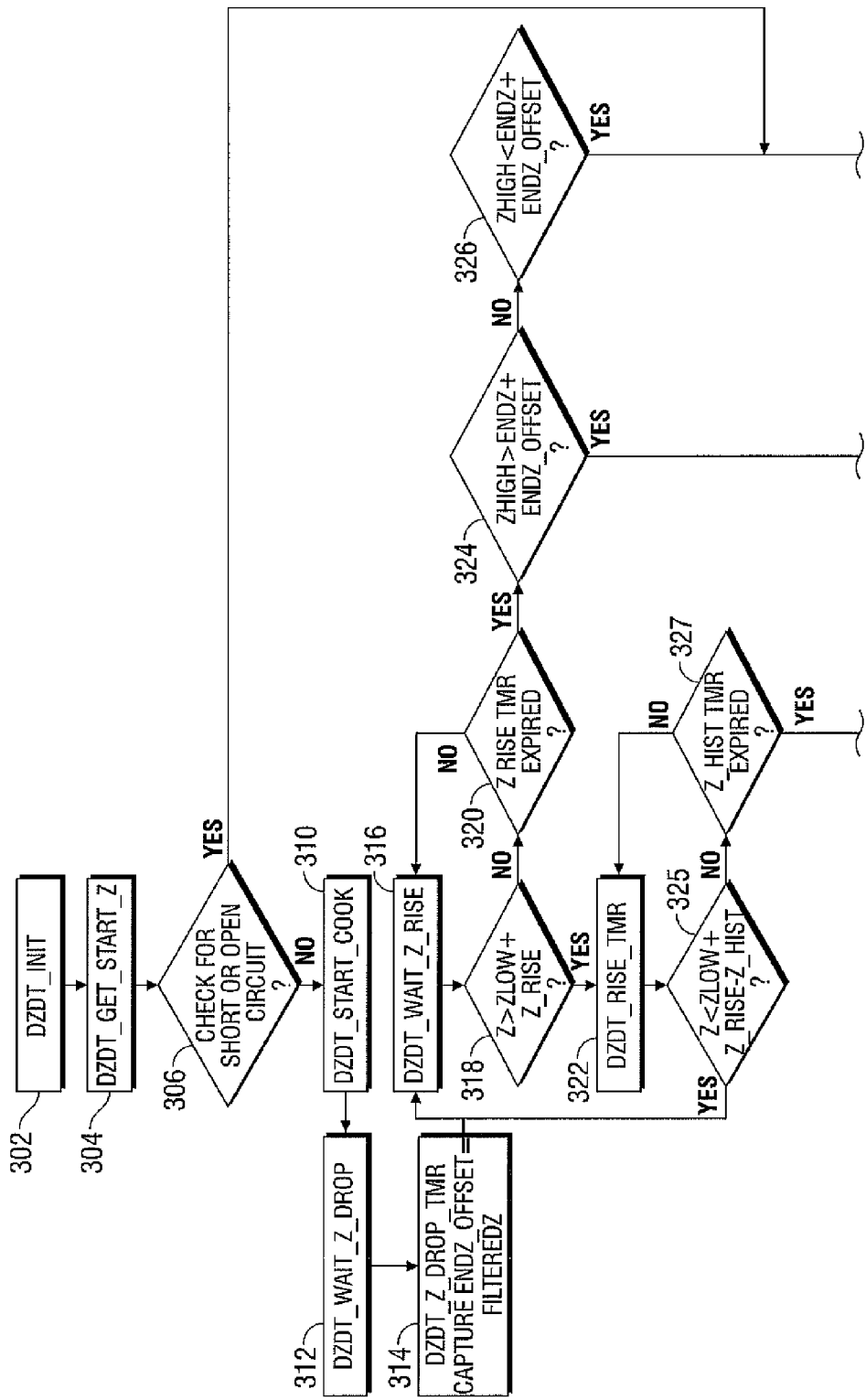
FIGS. 6A and 6B shows a flow chart showing a sealing method using the endoscopic bipolar forceps according to the present disclosure.
Figure 6B:
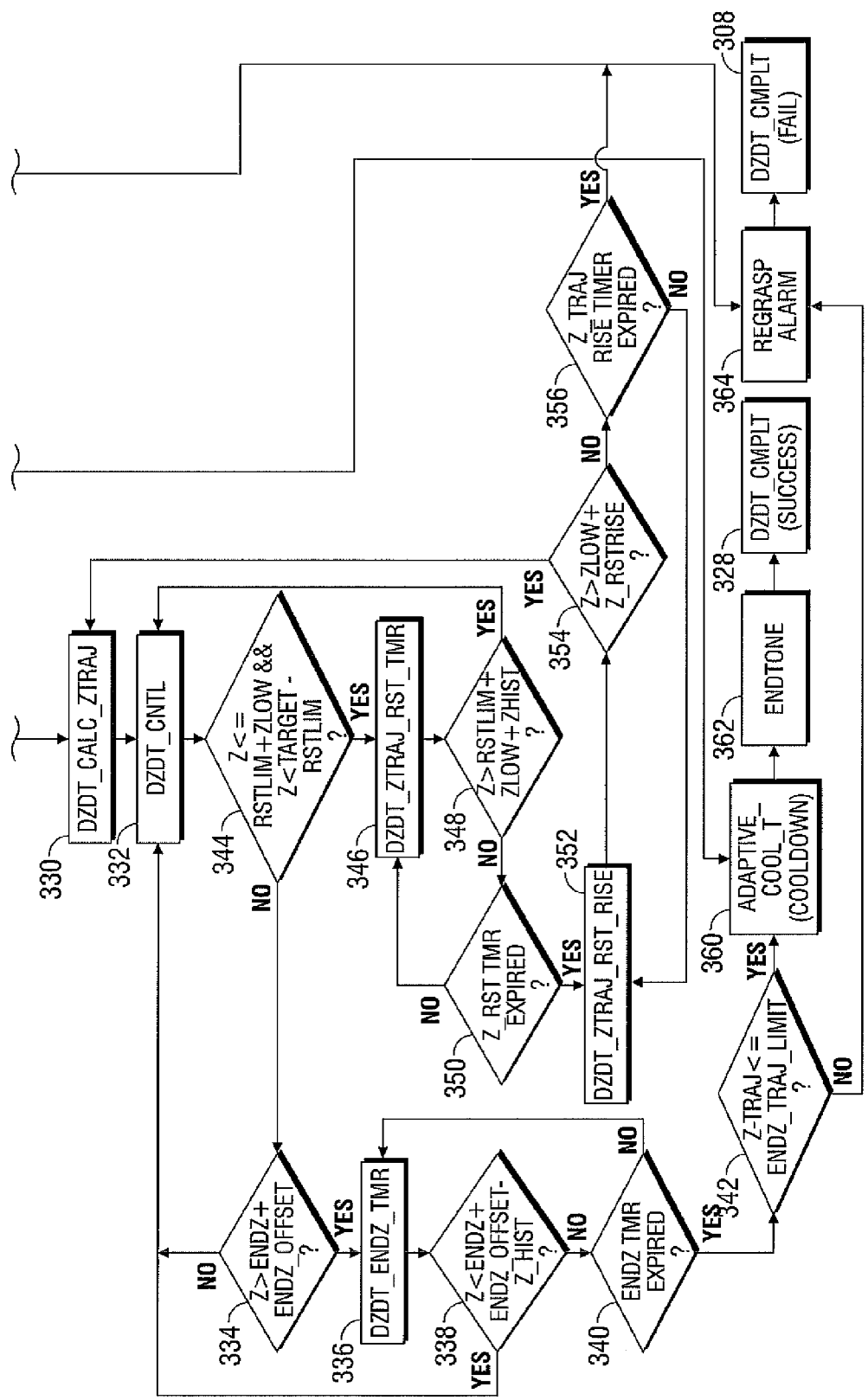
Figure 7:
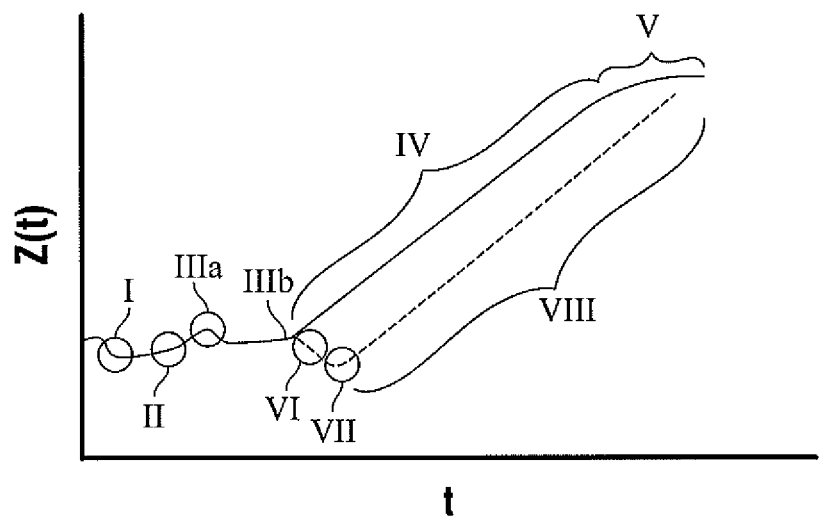
FIG. 7 shows a graph illustrating the changes occurring in tissue impedance during sealing utilizing the method shown in FIGS. 6A and 6B.

The method of sealing tissue according to the present disclosure is discussed below with reference to FIGS. 6A-B. In addition, FIG. 7 shows a graph illustrating the changes to tissue impedance when tissue is sealed utilizing the method of FIGS. 6A-B. The method is embodied in a software-based algorithm which is stored in memory 6 and is executed by processor 5.

In step 302, the vessel sealing procedure is activated (e.g., by pressing of a foot pedal or handswitch) and a host processor (e.g., processor 5) activates a vessel sealing algorithm and loads a configuration file. The configuration file may include a variety of variables which control the algorithm, e.g., end impedance threshold (EndZ), baseline cooling time (Base_Cool_T), and forceps/instrument identification (ForcepsID). Certain variables of the configuration file may be adjusted based on the instrument being used and the bar settings selected by a surgeon. A configuration file may be loaded from a data store included within controller 4. Additionally or alternatively, a configuration file may be loaded from a data store included within forceps 10. In embodiments a plurality of configuration files may be included within controller 4. A configuration file may be selected and loaded by the algorithm in accordance with the type of forceps being utilized, e.g., the ForcepsID. In embodiments, forceps 10 are interrogated by controller 4 to ascertain ForcepsID, whereupon a configuration file corresponding to ForcepsID is loaded. Base_Cool_T may be determined in accordance with ForcepsID.

In step 304, the algorithm begins with an impedance sense phase, shown as phase I in FIG. 7, during which the algorithm senses the tissue impedance with an interrogatory impedance sensing pulse of approximately 100 ms duration. The measured value of tissue impedance is stored as a variable DZDT_Start_Z. Tissue impedance is determined without appreciably changing the tissue. An adaptive cooling time (Adaptive_Cool_T) may be determined by adjusting the value indicated by Base_Cool_T in accordance with tissue impedance (DZDT_Start_Z). The cool-down time may be adjusted in accordance with additional or alternative factors as will be further described herein. During this interrogation or error-checking phase the generator 2 provides constant power to check for a short or an open circuit, in order to determine if tissue is being grasped. The cumulative (i.e., net amount) of energy delivered to the tissue during the sealing procedure may be stored in a variable (E_Total). E_Total may be determined in any suitable manner, for example without limitation, by integrating the output power over the power delivery time. In embodiments, the output power is sampled and totalized on a periodic basis to yield an approximation of total energy delivery. Processor 5 may be configured to execute an interrupt service routine (ISR) that is programmed to periodically sense and totalize cumulative output power (E_Eotal). Variables corresponding to the maximum energy delivery rate (E_Max), minimum energy delivery rate (E_Min), and an average energy delivery rate (E_Avg) may additionally or alternatively sensed and/or computed and stored.

Thermal properties related to the tissue may be sensed, recorded and/or computed during the sealing process. Such properties may include, without limitation, total thermal energy sensed, which may be expressed as the sensed temperature integrated over the time of the procedure (T_total), maximum tissue temperature (T_Max), minimum tissue temperature (T_Min), and average tissue temperature (T_Avg). Fluid properties, i.e., a total quantity of fluid, which may be expressed as the sensed quantity of fluid integrated over the time of the procedure (F_Total), a maximum fluid quantity (F_Max), a minimum fluid quantity (F_Min), and an average fluid quantity of fluid (F_Avg), may additionally or alternatively be sensed, recorded and/or computed.

In step 306, a determination is made whether the measured impedance is greater than a pre-programmed high impedance threshold, represented by the variable ImpSense_HiLimit, or less than a pre-programmed low impedance threshold, represented by the variable ImpSense_LowLimit. If in step 306 a short circuit is detected, e.g., impedance is below a low impedance threshold or if a an open circuit is detected, e.g., impedance is above a high impedance threshold, the algorithm in step 364 issues a regrasp alarm, and the algorithm exits in step 308. If, otherwise, no fault is detected in step 306 (i.e., no short and no open circuit detected), the algorithm starts the cook phase in step 310. The generator 2 then generates the pre-programmed ramping of current in its outer-loop and constant current per current curve within its inner-loop according to the current control curve shown in FIG. 8.

Figure 8:
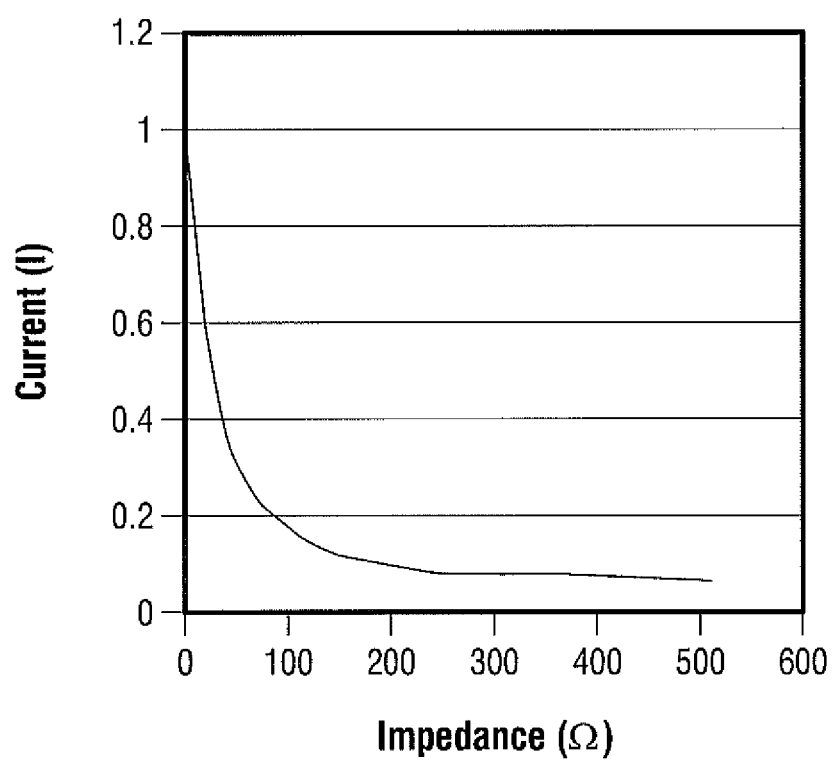
FIG. 8 shows a current v. impedance control curve according to the present disclosure.

The curve of FIG. 8 may be modified by intensity settings. In particular, selecting a specific intensity setting (e.g., low, medium, high, etc.) selects a corresponding value, represented by a variable, Cook_AmpMult, which then multiplies the curve. The Cook_AmpMult variable is specified in the configuration file and may range from about 2 Amps to about 5.5 Amps in some embodiments. In other embodiments, the Cook_AmpMult variable may range from about 2 Amps to about 8 Amps.

The control curve for this algorithm is designed as a current curve which decreases rapidly from low impedances to high, although it could also be represented as a power or voltage curve. The control curve is designed ideally to reduce power with increasing impedances higher than approximately 24 ohms. This shape provides several advantages: 1) this curve allows high power with low impedance tissues, which allows the tissue to heat rapidly at the start of the seal cycle; 2) this shape tames the positive feedback caused by increase in delivered power as a result of increasing impedance 3) the curve allows a slower control system for Z control as the output power is reduced as the impedance rises, thus keeping the tissue impedance from rising too quickly.

After the error checking phase, in step 310 the algorithm initiates application of the RF energy by delivering current linearly over time to heat the tissue. It is envisioned RF energy may be delivered in a non-linear or in a time-independent step manner from zero to an "on" state. Delivery may be controlled through other parameters such as voltage and/or power and/or energy. Once initiated, the ramping of energy continues until one of two events occurs: 1) the maximum allowable value is reached or 2) the tissue "reacts." The term "tissue reaction" is a point at which intracellular and/or extra-cellular fluid begins to boil and/or vaporize, resulting in an increase in tissue impedance. In the case when the maximum allowable value is reached, the maximum value is maintained until the tissue "reacts." In the event that the tissue reacts prior to reaching the maximum value, the energy required to initiate a tissue "reaction" has been attained and the algorithm moves to an impedance control state.

To identify that a tissue reaction has occurred, there are two elements which are considered. The first consideration is the minimum tissue impedance obtained during the heating period. In step 312, the algorithm continuously monitors the tissue impedance after the onset of energy to identify the lowest value reached and then in step 314 stores this value as the variable ZLow. As time progresses throughout the entire energy activation cycle, the stored value is updated anytime a new value is read that is lower than the previous Zlow, represented by phase II in FIG. 7. In other words, during steps 312, 314 and 316, the generator 2 waits for the tissue impedance to drop. The generator 2 also captures EndZ_Offset impedance, which corresponds to the initial measured tissue impedance. The EndZ_Offset impedance is used to determine the threshold for terminating the procedure. In step 314, EndZ_Offset impedance is measured approximately 100 ins after initial application of electrosurgical energy, which occurs approximately during phase I.

The second consideration in identifying tissue reaction is a predetermined rise in impedance. This is represented by the variable Z_Rise, which is loaded from the configuration file and can range from about 1 ohm to about 750 ohms. In step 316 the algorithm waits for a predetermined period of time to identify whether a rise in impedance has occurred, represented by phases IIIa and IIIb in FIG. 7. In step 318, the algorithm repeatedly attempts to identify a tissue reaction by determining if Z(t)>ZLow+Z_Rise where Z(t) is the impedance at any time during sampling. In step 320, the algorithm verifies whether the timer for waiting for impedance to rise has expired.

If the tissue does not rise within the predetermined period of time (e.g., in step 320 the timer has expired) then, the generator 2 issues a regrasp alarm due to the tissue not responding. In particular, in step 324 the generator 2 verifies whether the procedure is complete by comparing measured impedance to the impedance threshold. If the measured impedance is greater than the impedance threshold, the tissue is sealed and the electrosurgical energy (e.g., RF power) is shut off and the algorithm proceeds to step 360 wherein the cooling timer is activated.

In the step 360 the actual cooling time (Adaptive_Cool_T) is determined in accordance with the initial impedance (DZDT_Start_Z), final impedance (DZDT_End_Z), the instrument type (Forceps_ID), energy delivered to the tissue (i.e., E_total, E_Max, E_Min and/or E_Avg), thermal properties (i.e., T_total, T_Max, T_Min and/or T_Avg), and/or fluid properties (i.e., F_total, F_Max, F_Min and/or F_Avg). It is envisioned the actual cooling time may range from about zero seconds to about ten seconds. In embodiments, the actual cooling time may range from about a half a second to about two seconds. In embodiments, Adaptive_Cool_T is initially set to Base_Cool_T. Adaptive_Cool_T may then be increased or decreased in accordance with biologic or operational parameters. For example without limitation, Adaptive_Cool_T may be increased by an amount correlated to the extent by which a parameter exceeds a parameter threshold, and, conversely, Adaptive_Cool_T may be decreased by an amount correlated to the extent by which a parameter falls short of a parameter threshold. In embodiments, Adaptive_Cool_T may only be increased, or only decreased. In yet other embodiments, a parameter may cause an increase in Adaptive_Cool_T, a parameters may cause a decrease in Adaptive_Cool_T, and a parameter may cause both and increase and a decrease in Adaptive_Cool_T.

After the cooling period has expired and the endtone signaled, the sealing procedure ends with step 328, which prevents sealing tissue that has already been sealed.

If the tissue is not sealed, then in step 326 the generator determines whether the measured impedance is below the impedance threshold, and if so then the generator 2 issues a regrasp alarm in step 364 and exits in step 308.

To check for the reaction stability, the algorithm has a hysteresis identifier (Z_HIST) defined by a specified drop in impedance occurring in under a specified duration in time. This is used to filter out the noise which may be mistaken by the algorithm for the actual rise in impedance. In step 325, the algorithm determines whether the measured impedance is less than the rise in impedance above the lowest impedance minus the hysteresis identifier (i.e., Z(t)<Zlow+Z_Rise−Z_Hist). Step 325 is repeated for a specified period of time by determining whether a timer has expired in step 322 (Z_Hist tmr), the repetition of the loop is determined in step 327.

After the tissue reacts and tissue impedance begins to rise, if the impedance drops below a hysteresis value within an allotted time, the system identifies the event "not stable" as shown in phase IIIa. The algorithm also begins looking for the next rise in impedance by determining if the measured impedance is greater than the specified level of impedance, defined by the equation Z(t)<Zlow+Z_Rise−Z_Hist. If the timer expires and the impedance has not dropped below the hysteresis value, the reaction is considered stable and the impedance control state is implemented.

Once it is established that the tissue has reacted as shown in phase IIIb, the algorithm calculates the desired impedance trajectory based on the actual impedance and the desired rate of change in step 330. In step 332, the algorithm calculates a target impedance value for the control system at each time-step, based on a predefined desired rate of change of impedance (dZ/dt), represented as phase IV in FIG. 7. The desired rate of change may be stored as a variable and be loaded during the step 302. The control system then attempts to adjust the tissue impedance to match the target impedance. The target impedance takes the form of a target trajectory with the initial impedance value and time taken when the tissue reaction is considered real and stable. It is envisioned that the trajectory could take a non-linear and/or quasi-linear form. Thus, when the measured impedance is greater than the rise in impedance above lowest impedance (i.e., Z(t)>ZLow+ZRise), the algorithm calculates a Z trajectory based on the actual impedance and desired dZ/dt, i.e., a rate of rise of impedance over time, selected manually or automatically based on tissue type determined by the selected instrument.

The target impedance trajectory includes a plurality of a target impedance values at each time step. The algorithm drives tissue impedance along the target impedance trajectory by adjusting the power output level to substantially match tissue impedance to a corresponding target impedance value. While the algorithm continues to direct the RF energy to drive the tissue impedance to match the specified trajectory, the algorithm monitors the impedance to make the appropriate corrections. The algorithm determines whether tissue fusion is complete and the system should cease RF energy in phase V as shown in FIG. 7. This is determined by monitoring the actual measured impedance rising above a predetermined threshold and staying above the threshold for a predetermined period of time. The threshold is defined as a specified level, EndZ, above the initial impedance value, EndZ_Offset. This determination minimizes the likelihood of terminating electrosurgical energy early when the tissue is not properly or completely sealed.

In step 334, it is determined if the measured impedance is greater than as the specified level of impedance above the initial impedance value (i.e., Z(t)>EndZ+EndZ_Offset), if yes, the algorithm verifies whether this state is maintained for the given time. In step 336, the algorithm initializes the timer, DZDT_ENDZ_TIMER. In step 338, the algorithm performs the determination of step 334 for the duration of the timer DZDT_ENDZ_TIMER, which may be about 400 ms, the expiration of which is verified in step 340. If the sealing portion of the vessel sealing process (i.e., not including cool-down time) has exceeded a predetermined time period (e.g., maximum seal timer) which may be about 12 seconds, the algorithm exits with an alarm. This alerts the user to a possible unfused tissue condition.

It is envisioned that the EndZ value ranges from about 10 ohms to about 1000 ohms above the minimum impedance reached and EndZ_Offset is the tissue impedance approximately about 100 ms after the onset of RE energy. Further, the time duration for a cycle shut-off condition to verify tissue fusion has occurred, (i.e., the value of DZDT_ENDZ_TIMER) may range from 0 seconds to 2 seconds. It is also envisioned that the value of the EndZ_Offset could be calculated from a variety of different methods and utilizing a variety of different parameters such as the starting tissue impedance, the minimum impedance, the impedance at maximum current or minimum voltage, the impedance at either a positive or negative slope change of impedance, and/or a constant value specified within the programming or by the end user.

Once the timer expires and if the measured impedance is still above EndZ+EndZ_Offset the RF is shut off. However, it must be verified whether tissue reaction has not occurred too quickly (e.g., the control system failed to maintain control). This event is identified if the final measured impedance value deviated from the end target value by greater than a predetermined value, ENDZ_TRAJ_LIMIT. The ENDZ_TRAJ_LIMIT ranges from about 1 ohm to about 500 ohms. In step 342, the algorithm determines whether the measured impedance is below ENDZ_TRAJ_LIMIT. This event aids in mitigating the occurrences of the algorithm exiting while the tissue is not fused. If in step 342, the measured impedance is determined to be below ENDZ_TRAJ_LIMIT, then in step 360 the algorithm goes into a wait state having a duration in accordance with Adaptive_Cool_T to enable the fused tissue to set. After the expiration of the wait state, the algorithm in step 362 issues a seal complete signal, which may be an audio indication (i.e., an "endtone") and/or a visual indication, and in the step 328 the algorithm exits.

Prior to proceeding to step 334 to determine if the seal process is complete, the algorithm performs a plurality of error checks. In particular, the algorithm determines whether excessive fluid has entered the field or an object has been encountered that causes the impedance to drop unexpectedly to affect the ongoing tissue reaction. This event is identified by a negative deviation between the target impedance and tissue impedance (i.e. tissue impedance is less than target impedance) as represented by phase VI in FIG. 7. Therefore, to identify that this event has occurred and is real (e.g., not an arcing event) several conditions are verified. In step 344, the algorithm determines whether the impedance dropped below a reset threshold value, RstLim, above the lowest impedance reached, ZLow and whether the impedance deviated sufficiently from the target request. Therefore, this event is identified as: $Z(t)<=RstLim+ZLow$ & $Z(t)<target-RstLim$. It is recognized that the RstLim ranges from about 1 ohm to about 750 ohms. If no drop in impedance or deviation has occurred then the sealing process was successful and the algorithm proceeds to step 334 as discussed above. If a deviation has been detected, then in step 346 the algorithm performs a subsequent verification.

In step 346, at the onset of successfully meeting both of these conditions, the algorithm begins a timer, DZDT_ZTRAJ_RST_TMR, to define if the deviation event is true and stable or false and transient. In step 348, the algorithm determines whether the measured impedance is above the reset threshold value, RstLim, above the lowest impedance reached, ZLow plus a hysteresis value, ZHist. If this condition is satisfied before the timer DZDT_ZTRAJ_RST_TMR expires in step 350, the event is considered transient and the algorithm continues to direct the electrosurgical energy to cause the tissue impedance to follow the previous trajectory by returning to step 332.

If the condition described above in step 348 occurs and the timer expires in step 350, the event is deemed real and the algorithm proceeds to step 352 where the algorithm adjusts to look for tissue reaction as described earlier with respect to step 318. Specifically, in step 354, the impedance is monitored to identify a rise above the minimum value, Zlow, and once this occurs as represented by phase VII in FIG. 7, the trajectory is recalculated to begin at the new reaction impedance and the trajectory time is reset by returning to step 332 as represented by phase VIII in FIG. 7. The algorithm then continues with the same series of events described previously until tissue fusion is identified. If a rise in impedance is not detected in step 354 within a predetermined period of time then the algorithm proceeds to step 364 in which the algorithm issues a regrasp alarm, and in the step 308 the process concludes.

In normal operation, the algorithm directs the RF energy to maintain a match between the tissue impedance and the target value throughout time. Independent of the actual tissue impedance the target trajectory is incremented in a normal fashion during all events unless a reset trajectory is requested. However, it is also envisioned that the trajectory could enter a holding pattern with respect to the last value at any event when the actual tissue impedance deviates significantly from the target impedance until either a reset condition is requested or the tissue impedance realigns with the target value.

It is recognized that a number of methods not described here are possible to identify the condition described. The logic intent is to identify an event that results in notable and significant deviation from the impedance target by the tissue and thereby justifying a new target trajectory. Initializing a new trajectory results in mitigating excessive energy delivery to the tissue as the impedance deviates from the target and therefore prevents an uncontrollable tissue effect once the tissue re-reacts.

If during the initial RF energy ramp or during a negative deviation of tissue impedance from the target impedance, the tissue does not rise above the lowest measured impedance by a pre-defined amount within a pre-defined time then the algorithm will exit with an alarm. This alerts the user to a possible attempt to seal tissue which is already desiccated or sealed, an attempt to seal tissue which is so large that the tissue is not sufficiently affected by the RF energy delivered, an attempt to seal non-tissue, or a persistent short circuit during the sealing process.

The algorithm according to the present disclosure allows for the slow desiccation of tissue and for collagen to denature in a slow controllable fashion. As desiccation progresses, the resulting seal gains plastic-like qualities, becoming hard and clear, which makes the seal capable of withstanding higher burst pressures.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical tissue fusion system comprising:
   an electrosurgical instrument including at least one active electrode adapted to apply electrosurgical energy to tissue; and
   an electrosurgical generator adapted to supply electrosurgical energy to the at least one active electrode, the electrosurgical generator including:
   impedance sensing circuitry configured to measure impedance of tissue; and
   a processor configured to:
      regulate the supply of electrosurgical energy to tissue;
      determine whether a tissue reaction has occurred as a function of a minimum impedance value and a predetermined rise in impedance, wherein tissue reaction corresponds to a boiling point of tissue fluid, and wherein a timer is associated with the rise in impedance, an expiration of the timer setting off an alarm by the generator, the alarm prompting a re-grasp of tissue, whereas non-expiration of the timer triggers the generator to generate a ramping of current in an outer loop and a constant current in an inner loop of a current control curve;

determine a cooling period in response to the tissue reaction;

interrupt the supply of electrosurgical energy to tissue to effectuate the cooling period; and indicate expiration of the cooling period.

2. An electrosurgical tissue fusion system according to claim 1 wherein the electrosurgical instrument further includes: a pair of jaw members configured to grasp tissue; and a ratchet mechanism configured to selectively apply pressure to the jaws in response to the processor.

3. An electrosurgical tissue fusion system according to claim 2 wherein the processor is further configured to vary jaw pressure in response to a determination that tissue reaction has occurred.

4. An electrosurgical tissue fusion system according to claim 3 wherein jaw pressure is increased in response to a determination that tissue reaction has occurred.

5. An electrosurgical tissue fusion system according to claim 2 wherein the processor is further configured to increase jaw pressure upon activation of the electrosurgical energy.

6. An electrosurgical tissue fusion system according to claim 2 wherein the processor is further configured to vary jaw pressure in response to tissue impedance.

7. An electrosurgical tissue fusion system according to claim 2, wherein the processor is further configured to release jaw pressure upon expiration of the cooling period.

8. An electrosurgical tissue fusion system according to claim 1, wherein the processor is adapted to generate a threshold impedance value as a function of an offset impedance value and an ending impedance value, wherein the offset impedance value is obtained after an initial impedance measurement.

9. An electrosurgical tissue fusion system according to claim 8, wherein the processor is configured to determine whether tissue impedance is at least equal to the threshold impedance for a predetermined shutoff period.

10. An electrosurgical tissue fusion system according to claim 9, wherein the processor is configured to adjust output of the electrosurgical generator in response to the determination whether tissue impedance is at least equal to the threshold impedance for a predetermined shutoff period.

11. An electrosurgical tissue fusion system according to claim 1, wherein the electrosurgical instrument further includes an identification module.

12. An electrosurgical tissue fusion system according to claim 11, wherein the identification module includes at least one of a resistor, a barcode, an RFID tag, and computer memory.

13. An electrosurgical tissue fusion system according to claim 11, wherein electrode characteristics are encoded within the identification module.

14. An electrosurgical tissue fusion system according to claim 11, wherein the identification module is in operable communication with the processor.

15. An electrosurgical tissue fusion system according to claim 1, wherein the processor is configured to generate a target impedance trajectory as a function of measured impedance and desired rate of change based on the tissue reaction determination, the target impedance trajectory including a plurality of target impedance values.

16. An electrosurgical tissue fusion system according to claim 15, wherein the processor is configured to drive tissue impedance along the target impedance trajectory by adjusting the output level of the electrosurgical generator to substantially match tissue impedance to a corresponding target impedance value.

17. An electrosurgical tissue fusion system according to claim 1, wherein the cooling period is a fixed period of time.

18. An electrosurgical tissue fusion system according to claim 1, wherein the parameters relating to a tissue fusion process are selected from a group consisting of tissue temperature, tissue impedance, tissue mass, electrosurgical energy delivery, fluid presence, jaw angle, and electrode characteristics.

19. An electrosurgical tissue fusion system according to claim 1, wherein the cooling period ranges from about zero seconds to about ten seconds.

20. An electrosurgical tissue fusion system according to claim 1, wherein the cooling period ranges from about 0.5 seconds to about 2 seconds.

21. An electrosurgical tissue fusion system according to claim 1, wherein the processor is further configured to detect a hysteresis indicator to determine whether the tissue reaction is stable.

22. An electrosurgical tissue fusion system according to claim 1, wherein the indication is selected from the group consisting of an audible indication and a visual indication.

23. An electrosurgical tissue fusion system according to claim 1 wherein: the electrosurgical instrument further includes a jaw angle sensor in operable communication with the electrosurgical generator; and the processor is further configured to receive a signal from the jaw angle sensor and adjust at least one of the impedance trajectory and the cooling period in response thereto.

24. An electrosurgical tissue fusion system according to claim 1 wherein: the electrosurgical instrument further includes a temperature sensor in operable communication with the electrosurgical generator; and the processor is further configured to receive a signal from the temperature sensor and adjust at least one of the impedance trajectory and the cooling period in response thereto.

25. An electrosurgical tissue fusion system according to claim 1 wherein:

the electrosurgical instrument further includes a fluid sensor, configured to sense fluid at a surgical site, in operable communication with the electrosurgical generator; and the processor is further configured to receive a signal from the fluid sensor and adjust at least one of the impedance trajectory and the cooling period in response thereto.

* * * * *